United States Patent [19]

Kopolow et al.

[11] Patent Number: 5,169,622

[45] Date of Patent: * Dec. 8, 1992

[54] HAIR AND SKIN CARE COMPOSITIONS CONTAINING DISCRETE MICRODROPLETS OF AN OIL IN WATER STABILIZED BY IN SITU COPOLYMERIZATION OF A WATER-SOLUBLE VINYL MONOMER AND A WATER-SOLUBLE ACRYL COMONOMER

[75] Inventors: Stephen L. Kopolow, Plainsboro; William J. Burlant, Wayne; Michael W. Helioff, Westfield; Carmen D. Bires, Hackettstown; Robert B. Login, Oakland; Mohammed Tazi, Wayne, all of N.J.

[73] Assignee: ISP Investments Inc., Wilmington, Del.

[ * ] Notice: The portion of the term of this patent subsequent to Dec. 17, 2008 has been disclaimed.

[21] Appl. No.: 638,597

[22] Filed: Jan. 8, 1991

Related U.S. Application Data

[63] Continuation-in-part of Ser. No. 510,017, Apr. 17, 1990, abandoned, and a continuation-in-part of Ser. No. 604,263, Oct. 29, 1990, Pat. No. 5,073,296.

[51] Int. Cl.⁵ .......................... A61K 7/15; B01J 13/00
[52] U.S. Cl. ........................................ 424/47; 252/312; 252/89.1; 424/70; 424/73; 424/71; 424/59; 514/557; 514/772.7; 514/847
[58] Field of Search .............. 252/312, 70, 89.1; 424/73, 59, 71; 514/557, 772.7, 847

[56] References Cited

U.S. PATENT DOCUMENTS

| | | | |
|---|---|---|---|
| 4,923,695 | 5/1990 | Nowak, Jr. et al. | 424/71 |
| 4,933,170 | 6/1990 | Nowak, Jr. et al. | 424/67 |
| 4,940,576 | 7/1990 | Walsh | 424/70 |
| 5,034,220 | 7/1991 | Heliott et al. | 424/73 |

Primary Examiner—Richard D. Lovering
Assistant Examiner—N. Bhat
Attorney, Agent, or Firm—Walter Katz; Marilyn J. Maue; Joshua J. Ward

[57] ABSTRACT

What is provided herein are hair and skin care compositions containing discrete microdroplets of an oil in water stabilized by in situ polymerization of a water-soluble vinyl monomer and a water-soluble acryl comonomer. The stabilized microdroplets are prepared by dispersing the oil in water, adding the water-soluble vinyl monomer, preferably vinylpyrrolidone, with the comonomer, and copolymerizing the monomer and comonomer in situ such that the oil is stabilized in the resulting copolymer solution as discrete microdroplets.

17 Claims, No Drawings

HAIR AND SKIN CARE COMPOSITIONS CONTAINING DISCRETE MICRODROPLETS OF AN OIL IN WATER STABILIZED BY IN SITU COPOLYMERIZATION OF A WATER-SOLUBLE VINYL MONOMER AND A WATER-SOLUBLE ACRYL COMONOMER

CROSS-REFERENCE TO RELATED PATENT APPLICATIONS

This application is a continuation-in-part of copending U.S. patent applications, Ser. No. 510,017, filed Apr. 17, 1990, now abandoned and Ser. No. 604,263, filed Oct. 29, 1990, U.S. Pat. No. 5,073,296 and assigned to the same assignee as herein.

BACKGROUND OF THE INVENTION

1. Field of the Invention

This invention relates to hair and skin compositions containing oils in water, and more particularly, to such compositions containing stable, discrete microdroplets of an oil in water stabilized by a water-soluble copolymer solution.

2. Description of the Prior Art

The unique properties of many oils make it desirable to include them in aqueous-based hair and skin compositions. For example, cosmetically-active materials such as silicone oils, fluids and gums, mineral oils, and water-insoluble organic esters such as isopropropyl palmitate and isopropyl myristate, are particularly useful in cosmetic formulations for the skin and hair. In such compositions, their lubricity properties impart conditioning action for the user. However, such oils are immiscible with water which makes it very difficult to maintain a stable aqueous dispersion without rapid separation of the composition into oil and water phases. To solve the problem of providing effective dispersibility of such materials in water, it has been necessary to include a surfactant in aqueous cosmetic compositions containing cosmetically-active oils in order to maintain dispersed droplets of the oil in the aqueous solution. However, the use of surfactants increases the cost of the product and may effect the quality of the composition. In addition, even with a surfactant present, the stability of the dispersion is often not completely satisfactory. See, for example, U.S. Pat. Nos. 3,957,970; 4,472,375; 4,559,227; 4,586,518; 4,728,457; 4,741,855; 4,749,565; 4,749,732; 4,788,006; and 4,849,127.

However, these and other processes have not provided a composition in which cosmetically active oils, such as silicone oils, are present as a stable dispersion in an aqueous medium. Nor does the prior art suggest a procedure for allowing such oils to maintain themselves in stable condition in an aqueous cosmetic formulation.

Accordingly, it is an object of the present invention to provide a cosmetic composition having a stabilized oil in water therein, preferably in the form of microdroplets, which can be maintained discretely and for an extended period of time.

Another object of this invention is to provide a method for preparing an aqueous hair or skin care composition which includes stable, discrete microdroplets of a silicone oil dispersed therein.

Still another object of the present invention is to provide a method of preparing a hair or skin care composition in which microdroplets of silicone oil are homogeneously distributed in the composition.

Yet another object is to provide a hair and skin care composition in which stable, dispersed microdroplets are prepared by in situ copolymerization of a water-soluble vinyl monomer, such as vinylpyrrolidone, and a water soluble acryl comonomer, in the presence of dispersed droplets of a water-insoluble oil, such as silicone oil, in water.

Among the other objects of the invention is to provide a hair or skin care formulation containing stable, discrete microdroplets of a cosmetically-active oil stabilized in an aqueous solution of in situ copolymerized vinylpyrrolidone monomer and methacrylamidopropyltrimethylammonium chloride comonomer.

These and other objects and features of the invention will be made apparent from the following description thereof.

ABBREVIATIONS AND DEFINITIONS

Oil—A compound which is a water-insoluble liquid at room temperature and has an oily consistency
Cosmetically-active oil—An oil which imparts a particularly desirable property, e.g. lubricity, to a cosmetic formulation
VP—Vinylpyrrolidone
PVP—Polyvinylpyrrolidone
Acryl Comonomer—a water-soluble acrylic, acrylate, acrylamide monomer, quaternized or unquaternized, e.g. a quaternized amino acrylamide
MAPTAC—Methacrylamidopropyltrimethylammonium chloride
DM—Polydimethylsiloxane, Dimethicone, 100 cs, Petrarch Chem. Co; 1000 cs, Dow Corning Corp.
MO—Mineral oil
TBP—Tert-butyl peroctoate, e.g. Trigonox® 21 (AKZO Chem. Co.)
TBPP—t-Butylperoxy pivalate, e.g. Lupersol 11 (Atochem N.A.)
Brookfield viscosity—Viscosity of Stabilized Oil in Water Product in cps, as measured using a RVT spindle #3 @ 70 rpm

SUMMARY OF THE INVENTION

What is provided herein is a cosmetic composition for the care of the hair or skin containing stable, discrete microdroplets of a cosmetically-active oil in water stabilized in a copolymer solution of an in situ copolymerized, water-soluble vinyl monomer and a water-soluble acryl comonomer. The stable, discrete, microdroplets are prepared by dispersing the oil in water to form microdroplets, adding a water-soluble vinyl monomer, such as vinylpyrrolidone, a water-soluble acryl comonomer, such as methacrylamidopropyltrimethylammonium chloride, and copolymerizing the monomer and comonomer in situ such that the oil droplets are stabilized in the resultant aqueous copolymer solution.

In the preferred form of the invention, the cosmetically-active oil is a silicone oil, a mineral oil or a water-insoluble ester such as isopropyl myristate and isopropyl palmitate.

Suitably the dispersion is present in an amount of about 0.1 to 25 weight percent of the composition, preferably about 1 to 10 weight percent, of the hair or skin care composition.

DETAILED DESCRIPTION OF THE INVENTION

The active material to be dispersed is a cosmetically-active oil which is a water-insoluble liquid at room temperature, and which imparts a particularly desirable property to hair or skin care cosmetic formulations. Such cosmetically-active oils include silicone oils, mineral oils and water-insoluble esters such as isopropyl myristate and isopropyl palmitate.

Suitable silicone oils or fluids for use in the invention may be selected from non-volatile polyalkyl siloxanes, polyaryl siloxanes, polyalkylaryl siloxanes and polyether siloxane copolymers. Mixtures of these compounds also may be used as long as the final mixture is non-volatile and the dispersed silicone particles are insoluble in the aqueous medium. As used herein, "insoluble" requires that the oil does not substantially dissolve in water and is essentially immiscible therewith.

Non-volatile polyalkylsiloxanes include, for example, polydimethylsiloxanes (Dimethicone) with viscosities ranging from about 5–600,000 centistokes (cs) at 25° C. These siloxanes are available, for example, from the General Electric Company as the VISCASIL series and from Dow Corning as the Dow Corning 200 products. Their viscosity can be measured by the glass capillary viscometer procedure set forth in Dow Corning Corporate Test Method CTM 0004 issued Jul.20, 1970. Preferably, the viscosity of these siloxanes selected have a viscosity of about 100 to about 100,000 cs, and most preferably, a viscosity of up to about 15,000 cs.

Suitable non-volatile polyalkylarylsiloxanes include, for example, polymethylphenylsiloxanes having viscosities of about 15 to 65 cs at 25° C. These siloxanes are available, for example, from the General Electric as SF 1075 methylphenyl fluid or from Dow Corning as 556 Cosmetic Grade Fluid. Additionally, poly(dimethylsiloxane) (diphenylsiloxane) copolymers having a viscosity in the range of about 10 to 100,000 cs at 25° C. are useful.

These and other suitable silicones are disclosed in U.S. Pat. Nos. 2,826,551, 3,964,500 and 4,364,837; and British Patent 849,433. The disclosures of these patents are incorporated by reference herein, as is the booklet "Silicone Compounds", which was distributed by Petrarch Systems Inc. in 1984, and which describes the preparation and properties of available silicones for use in this invention.

Other suitable oils for use herein include cosmetically-active materials such as light and heavy mineral oils, and water-insoluble organic esters such as isopropyl palmitate and isopropyl myristate.

In the practice of the present invention, the oil to be dispersed is first added to water and then subjected to agitation to produce a fine dispersion of discrete oil microdroplets throughout the aqueous medium. The mixture is agitated sufficiently so that the dispersion is stable for a period of at least 5 to 10 minutes without separating into individual layers. Conventional laboratory and high speed agitators may be used for this purpose, as for example, conventional anchor or wide-span turbine agitators.

Thereafter, a water-soluble vinyl monomer, for example, a vinylpyrrolidone monomer, such as vinylpyrrolidone itself, or a derivative thereof, such as an alkyl vinyl pyrrolidone, and as water-soluble acryl comonomer, such as methacrylamidopropyltrimethylammonium chloride, are added to the mixture, along with an appropriate free radical polymerization initiator.

Suitable free radical polymerization initiators for polymerization of water-soluble vinyl and acryl monomers include such free radical catalysts as t-butylperoctoate, t-butylperoxy- pivalate and the like. Oil-soluble catalysts are preferred.

Thereafter, the reaction mixture is maintained at a temperature in the range of about 55° to 85° C., preferably, about 75° to 85° C., and most preferably, about 78° to 82° C., for a period of time sufficient to effect the desired polymerization and form the aqueous polymer solution necessary to stabilize the discrete microdroplets of the oil.

As the polymerization proceeds, the dispersed oil droplets become white and appear to precipitate in the aqueous medium, however, without coalescing. Generally, the observance of this white or milky color in the aqueous medium is an indication of completion of the process, which usually takes about 2 to 20 hours, preferably about 4 to 10 hours, and most preferably, about 6 to 8 hours. After completion of polymerization, the residual vinyl monomer content generally is less than about 0.1%, as measured by the iodine titration method.

The production of stable, discrete microdroplets of oil in the resulting aqueous copolymer solution can be controlled by the viscosity of the aqueous copolymer solution. For example, the viscosity of this medium can be increased by increasing the relative amount of vinyl monomer to oil in the original reaction mixture. By increasing the viscosity of the copolymer solution, the tendency to form a stable, homogeneous suspension of discrete microdroplets of oil throughout the entire medium is enhanced. On the other hand, reducing the viscosity of the medium by decreasing the amount of vinyl monomer in the initial mixture results in a more dilute concentration of polyvinyl copolymer in the resultant mixture, which enhances the tendency to form a separate layer of discrete oil droplets.

Suitably, the ratio of monomer and comonomer to oil used in the polymerization should be in the range of about 95/5 to 5/95, respectively, on a weight basis, preferably at least about 50/50. Most preferred is a range of about 90/10 to 70/30. As used herein, a "stable composition or suspension" means that the discrete oil microdroplets remain suspended in the aqueous polymer solution for at least seven days at ambient temperature.

The viscosity of the stabilized oil in water product, for example, polyvinylpyrrolidone copolymer which is, obtained by in situ polymerization of vinylpyrrolidone monomer, and acryl comonomer, suitably is in the range of about 3,000 to 100,000 cps, preferably about 4,000 to 60,000 cps, and most preferably, about 6,000 to 25,000 cps.

The diameter of the oil microdroplets obtained are observed to be in the range of about 0.1 to 450 microns, and usually are about 1 to 100 microns.

The hair and skin care cosmetic compositions in accordance with the present invention containing the discrete, cosmetically-active oil dispersion as defined above can be provided under different forms.

The hair and skin care cosmetic compositions according to the invention can contain the dispersion either as the principal active component or as an additive.

Moreover, these compositions generally contain at least one conventional adjuvant used in cosmetic compositions.

The hair and skin care cosmetic compositions can be provided in the form of aqueous, alcoholic or hydroalcoholic solutions, the alcohol being principally a lower alkanol such as ethanol or isopropanol, or in the form of a cream, a gel, an emulsion or even in the form of an aerosol packaged under pressure in an aerosol container together with a propellant.

The adjuvants generally provided in the cosmetic compositions according to the invention are, for example, perfumes, dyes, preservatives, sequesterants, thickening agents and the like.

The cosmetic compositions according to the invention are either compositions ready for use or concentrates which can be diluted before use.

The cosmetic compositions according to the invention are not limited to a particular concentration of the dispersion described above. However, generally, in the cosmetic compositions according to the invention, the concentration of the PVP-silicone oil dispersion is between 0.1 and 25 weight percent and preferably between 1 and 10 weight percent.

As has been indicated above, the dispersion of the cosmetically-active oil in the cosmetic composition of the invention imparts principally advantageous cosmetic characteristics when they are applied to the hair or skin of the user.

The hair and skin care cosmetic compositions in accordance with the invention are characterized by the fact that they contain stable, discrete microdroplets of a cosmetically-active oil in the form of a dispersion.

These cosmetic compositions for the hair and skin can be provided in the form of aqueous, alcoholic or hydroalcoholic solutions, the alcohol being either ethanol or isopropanol, preferably in the form of a cream, a mousse, a lotion, an oil, a water-in-oil emulsion or even in the form of a spray. In this latter case, the compositions are packaged in an aerosol container, under pressure, together with a propellant such as nitrogen, nitrous oxide, carbon dioxide, butane or even mixtures of such propellants.

As has been indicated above, the cosmetic composition according to this invention is preferably employed for the care or treatment of the hair or skin.

In skin use, these compositions facilitate the hydration of the skin and avoid its drying out. These compositions also impart to the skin excellent softness to the touch.

The cosmetic compositions for the skin are provided preferably in the form of lotions, creams, gels, emulsions, mousses or aqueous, alcoholic or hydroalcoholic solutions.

The adjuvants generally present in these cosmetic compositions are, for example, perfumes, dyes, preservatives, thickening agents, sequesterants, emulsifiers, solar filters and the like.

These compositions for the skin constitute principally treating creams or lotions for the hands, face or body, sunscreens, and cleansing lotions.

These compositions are prepared according to known methods.

For example, to obtain a cream, an aqueous phase containing in solution the dispersion and optionally other components or adjuvants is emulsified with an oily phase.

The oily phase can be constituted by various compounds such as, for example, paraffin oil, petrolatum oil, sweet almond oil, avocado oil, olive oil, esters of fatty acids such as glyceryl monostearate, ethyl or isopropyl palmitates, alkyl myristates such as propyl, butyl or cetyl myristates. Fatty alcohols such as cetyl alcohol or waxes such as beeswax can also be added.

What is also provided herein is a conditioning hair care composition comprising (a) a stabilized silicone product obtained by in situ copolymerization of a water-soluble vinyl monomer, preferably vinylpyrrolidone, and a water-soluble acryl comonomer, preferably MAPTAC, in the presence of discrete microdroplets of a silicone oil in water, (b) a surfactant, and the balance being (c) water.

Surfactants

The surfactants useful in the conditioning hair care compositions of this invention can be present at a level of from about 1% to about 30%, most preferably from about 5% to about 25% of the composition. Surfactants useful in compositions of the invention include anionic, nonionic, cationic, zwitterionic and amphoteric surfactants.

Synthetic anionic detergents useful herein, particularly for the shampoo compositions, include alkyl and alkyl ether sulfates. These materials have the respective formulae $ROSO_3M$ and $RO(C_2H_4O)_xSO_3M$ where R is alkyl or alkenyl of about 10 to about 20 carbon atoms, x is 1 to 10, and M is a water-soluble cation such as ammonium, sodium, potassium and triethanolamine. The alkyl ether sulfates useful in the present invention are condensation products of ethylene oxide and monohydric alcohols having about 10 to about 20 carbon atoms. Preferably, R has 12 to 18 carbon atoms in both the alkyl and alkyl ether sulfates. The alcohols can be derived from fats, e.g., coconut oil or tallow, or can be synthetic. Lauryl alcohol and straight chain alcohols derived from coconut oil are preferred herein. Such alcohols are reacted with 1 to 10, and especially 3, molar proportions of ethylene oxide and the resulting mixture of molecular species, having, for example, an average of 3 moles of ethylene oxide per mole of alcohol, is sulfated and neutralized.

Specific examples of alkyl ether sulfates of the present invention are sodium coconut alkyl triethylene glycol ether sulfate; lithium tallow alkyl triethylene glycol ether sulfate; and sldium tallow alkyl hexaoxyethylene sulfate. Highly preferred alkyl ether sulfates are those comprising a mixture of individual compounds, said mixture having an average alkyl chain length of from about 12 to 16 carbon atoms and an average degree of ethoxylation of from about 1 to 4 moles of ethylene oide. Such a mixture also comprises from about 0 to 20% by weight $C_{12-13}$ compounds; from 60 to 100% by weight of $C_{14-15-16}$ compounds, from about 0 to 20% by weight of $C_{17-18-19}$ compounds; from about 3 to 30% by weight of compounds having a degree of ethoxylation of 0; from about 45 to 90% by weight of compounds having a degree of ethoxylation of from 1 to 4; from about 10 to 25% by weight of compounds having a degree of ethoxylation of from 4 to 8; and from about 0.1 to 15% by weight of compounds having a degree of ethoxylation greater than 8.

Another suitable class of anionic surfactants are the water-soluble salts of the organic, sulfuric acid reaction products of the general formula:

$$R_1-SO_3-M$$

wherein $R_1$ is chosen from the group consisting of a straight or branched chain, saturated aliphatic hydrocarbon radical having from 8 to 24, preferably 12 to 18, carbon atoms; and M is a cation. Important examples are the salts of an organic sulfuric acid reaction product of a hydrocarbon of the methane series, including iso-, neo-, ineso-, and n-paraffins, having 8 to 24 carbon atoms, preferably 12 to 18 carbon atoms and a sulfonating agent e.g., $SO_3$, $H_2SO_4$ oleum, obtained according to known sulfonation methods, including bleaching and hydrolysis. Preferred are alkali metal and ammonium sulfonated $C_{12\text{-}18}$ n-paraffins.

Additional examples of anionic synthetic detergents which come within the terms of the present invention are the reaction products of fatty acids esterified with isethionic acid and neutralized with sodium hydroxide where, for example, the fatty acids are derived from coconut oil; sodium or potassium salts of fatty acid amines of methyl tauride in which the fatty acids, or example, are derived from coconut oil. Other anionic synthetic detergents of this variety are set forth in U.S. Pat. Nos. 2,486,921; 2,486,922; and 2,396,278.

Still other anionic synthetic detergents include the class designated as succinamates. This class includes such surface active agents as disodium N-octadecylsulfosuccinamate, tetrasodium N-(1,2-dicarboxyethyl)-N-octadecylsulfo-succinamate, diamyl ester of sodium sulfosuccinic acid; dihexyl ester of sodium sulfosuccinic acid; dioctyl esters of sodium sulfosuccinic acid.

Other suitable anionic detergents utilizable herein are olefin sulfonates having about 12 to about 24 carbon atoms. The term "olefin sulfonates" is used herein to mean compounds which can be produced by the sulfonation of alpha-olefins by means of uncomplexed sulfur trioxide, followed by neutralization of the acid reaction mixture in conditions such that any sultones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form.

The alpha-olefins from which the olefin sulfonates are derived are mono-olefins having 12 to 24 carbon atoms, preferably 14 to 16 carbon atoms. preferably, they are straight chain olefins. Examples of suitable 1-olefins include 1-dodecene; 1-tetradecene; 1-hexadecene; 1-octadecene; 1-eicosene and 1-tetracosene.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

A specific alpha-olefin sulfonate mixture of the above type is described more fully in the U.S. Pat. No. 3,332,880 of Phillip F. Pflaumer and Adrian Kessler, issued Jul. 25, 1967, titled "Detergent Composition", the disclosure of which is incorporated herein by reference.

Another class of anionic organic detergents are the beta-alkyloxy alkane sulfonates. There compounds have the following formula:

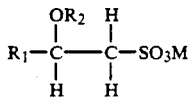

where $R_1$ is a straight chain alkyl group having from 6 to 20 carbon atoms, $R_2$ is a lower alkyl group having from 1 (preferred) to 3 carbon atoms, and M is a water-soluble cation as hereinbefore described.

Many additional nonsoap synthetic anionic surfactants are described in McCutcheon's, DETERGENTS AND EMULSIFIERS, ANNUAL, published by Allured Publishing Corporation, which is incorporated herein by reference. Also, U.S. Pat. No. 3,929,678, to Laughlin et al., issued Dec. 30, 1975 discloses many other anionic as well as other surfactant types and is incorporated herein by reference.

Nonionic surfactants, which are preferably used in combination with an anionic, amphoteric or zwitterionic surfactant, can be broadly defined as compounds produced by the condensation of alkylene oxide groups (hydrophilic nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration, with ethylene oxide, e.g., a coconut alcohol ethylene oxide condensate having from 10 to 30 moles of ethylene oxide per mole of coconut alcohol, the coconut alcohol fraction having from 10 to 14 carbon atoms.

4. Long chain tertiary amine oxides corresponding to the following general formula:

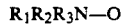

wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyldodecylamine oxide, oleyldi(2-hydroxyethyl) amine oxide, dimethyloctylamine oxide, dimethyl-decylamine oxide, dimethyltetradecylamine oxide, 3,6,9-trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl)amine oxide, dimethylhexadecylamine oxide.

5. Long chain tertiary phosphine oxides corresponding to the following general formula:

$$RR'R''P{\rightarrow}O$$

wherein R contains an alkyl, alkenyl or monohydroxyalkyl radical ranging from 8 to 18 carbon atoms in chain length, from 0 to about 10 ethylene oxide moieties and from 0 to 1 glyceryl moiety and R' and R'' are each alkyl or monohydroxyalkyl groups containing from 1 to 3 carbon atoms. The arrow in the formula is a conventional representation of a semipolar bond. Examples of suitable phosphine oxides are: dodecyldimethylphosphine oxide, tetradecyldimethylphosphine oxide, tetradecylmethylethylphosphine oxide, 3,6,9,-trioxaoctadecyldimethylphosphine oxide, cetyldimethylphosphine oxide, 3-dodecoxy-2-hydroxypropyldi(2-hydroxyethyl) phosphine oxide, stearyldimethylphosphine oxide, cetylethylpropylphosphine oxide, oleyldiethylphosphine oxide, dodecyldiethylphosphine oxide, tetradecyldiethylphosphine oxide, dodecyldipropylphosphine oxide, dodecyldi(hydroxymethyl)phosphine oxide, dodecyldi(2-hydroxypropyl)phosphine oxide, oleyldimethylphosphine oxide, 2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contain alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include: octadecyl methyl sulfoxide, 2-ketotridecyl methyl sulfoxide, 3,6,9-trioxaoctadecyl 2-hydroxyethyl sulfoxide, dodecyl methyl sulfoxide, oleyl 3-hydroxypyropyl sulfoxide, tetradecyl methyl sulfoxide, 3-methoxytridecyl methyl sulfoxide, 3-hydroxytridecyl methyl sulfoxide, 3-hydroxy-4-dodecoxybutyl methyl sulfoxide.

Zwitterionic surfactants, useful in shampoos, can be exemplified by those which can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

$$R^2-Y^{(+)}\overset{(R^3)_x}{|}-CH_2-R^4-Z^{(-)}$$

wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; $R^3$ is an alkyl or monohydroxyalkyl group containing 1 to about 3 carbon atoms; X is 1 when Y is a sulfur atom and 2 when Y is a nitrogen or phosphorus atom; $R^4$ is an alkylene or hydroxyalkylene of from 1 to about 4 carbon atoms and Z is a radical selected from the group consisting of carboxylate, sulfonate, sulfate, phosphonate, and phosphate groups.

Examples include:
4-[N,N-di(2-hydroxyethyl)-N-octadecylammonio]-butane-1-carboxylate; 5-[S-3-hydroxypropyl-S-hexadecylsulfonio]-3-hydroxypentane, -1-sulfate;pO 3-[P,P-diethyl-P-3,6,9-trioxatetradexocyl-phosphonio]-2-hydroxypropane-1-phosphate;

3-[N,N-dipropyl-N-3-dodecoxy-2-hydroxypropylammonio]-propane -1-phosphonate;

3-(N,N-dimethyl-N-hexadecylammonio)propane-1-sulfonate;

3-(N,N-dimethyl-N-hexadecylammonio)-2-hydroxypropane -1-sulfonate;

4-[N,N-di(2-hydroxyethyl)-N-(2-hydroxydodecyl)ammonio]-butane-1-carboxylate;

3-[S-ethyl-S-(3-dodecoxy-2-hydroxypropyl)sulfonio]-propane-1-phosphate;

3-[P,P-dimethyl-P-dodecylphosphonio]-propane-1-phosphate; and

5-[N,N-di(3-hydroxypropyl)-N-hexadecylammonio]-2-hydroxypentane-1-sulfate.

Other zwitterionics such as betaines are also useful in the present invention. Examples of betaines useful herein include the high alkyl betaines such as coco dimethyl carboxymethyl betaine, lauryl dimethyl carboxymethyl betaine, lauryl dimethyl alphacarboxyethyl betaine, cetyl dimethyl carboxymethyl betaine, lauryl bis-(2-hydroxy-ethyl) carboxy methyl betaine, stearyl bis-(2-hydroxy-propyl) carboxymethyl betaine, oleyl dimethyl gamma-carboxypropyl betaine, lauryl bis-(2-hydroxypropyl) alpha-carboxyethyl betaine, etc. The sulfobetaines may be represented by coco dimethyl sulfopropyl betaine, stearyl dimethyl sulfopropyl betaine, lauryl dimethyl sulfoethyl betaine, lauryl bis-(2-hydroxy-ethyl) sulfopropyl betaine and the like; amido betaines and amidosulfobetaines, wherein the $RCONH(CH_2)_3$ radical is attached to the nitrogen atom of the betaine are also useful in this invention. The amido betaines are preferred for use in some of the compositions of this invention.

Sultaine compounds described in "Encyclopedia of Shampoo Ingredients" may also be used.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylammopropane sulfonate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528,378.

The above-mentioned surfactants can be used alone or in combination in the hair care compositions of the present invention. the alkyl sulfates, the ethoxylated alkyl sulfates and mixtures thereof are preferred for use herein.

WATER

Water is an essential component of the present invention's compositions and generally comprises from about 20% to about 98% of the total composition.

OPTIONAL COMPONENTS

The present compositions herein can contain a variety of other optional components suitable for rendering such compositions more acceptable. Such conventional optional ingredients are well known to those skilled in the art, e.g., pearlescent aids such as ethylene glycol distearate; preservatives such as benzyl alcohol, methyl paraben, propyl paraben and imidazolidinyl urea; thickeners and viscosity modifiers such as a diethanolamide of a long chain fatty acid (e.g., lauric diethanolamide), cocomonoethanol amide, dimethicone copolyols, guar gum, methyl cellulose starches and starch derivatives, fatty alcohols such as cetearyl alcohol, sodium chloride, sodium sulfate, polyvinyl alcohol, and ethyl alcohol; pH adjusting agents such as citric acid, lactic acid, sodium citrate, succinic acid, phosphoric acid, sodium hydroxide, sodium carbonate, etc.; coloring agents such as any of the FD&C or D&C dyes; hair oxidizing (bleaching) agents such as hydrogen peroxide, perborate and persulfate salts; hair reducing agents such as the thioglycolates; perfumes; and, sequestering agents such as disodium/tetrasodium ethylenediamine tetraacetate, polymer plasticizing agents such as glycerin and propylene glycol. Such agents generally are used individually at a level of from about 0.01% to about 10%, preferably from about 0.05% to about 5.0% by weight of the composition.

The pH of the present compositions is not critical and may be in the range of from about 3.5 to about 8.0.

As with all compositions, the present compositions should not contain components which unduly interfere with the performance of the compositions.

EXAMPLE 1

The in situ polymerization process of the invention was carried out in a 1-liter laboratory reactor equipped with an overhead stirring motor, a metal anchor agitator, a nitrogen gas inlet tube, a water condenser connected to a bubbler, a temperature probe connected to a temperature controller and associated with a heating mantle, and a dropping funnel.

The reactor first was purged with nitrogen and charged with 400 g. of distilled water and 10 g. of Dimethicone oil having a viscosity of 100 cs. The oil-water then mixture was agitated vigorously at 350 rpm under nitrogen for 30 minutes whereupon the oil was dispersed as transparent, discrete microdroplets in the aqueous medium. The dispersion then was heated to 80° C. and 0.25 g. of di-tert-butylperoctoate was added. At this point, the mixture was maintained for 30 minutes with continuous stirring whereafter 90 g. of vinylpyrrolidone and an additional 0.25 g. of di-tert-butylperoctoate was added at one time while maintaining a nitrogen flow of 15 ml/min. After about 10–15 minutes, an exotherm was observed and the temperature increased to 86° C. The transparent, spherical droplets of oil became opaque. The the temperature was reduced to 80° C. and polymerization was continued for 6–8 hours with stirring. During this period, the dispersion became milky and the droplets became completely invisible. Polymerization was considered complete when the measured residual monomer content was less than 0.1%.

The composition obtained was a stable, homogeneous dispersion of microdroplets of Dimethicone oil stabilized in an aqueous polyvinylpyrrolidone solution. Upon exerting only slight pressure on the microdroplets, the silicone oil was observed to ooze out. However, the composition was quite stable for many months at room temperature, and for an extended period at the elevated temperature of 45° to 54° C.

EXAMPLES 2-3

The procedure of Example 1 was repeated using weight ratios of 80 g. of vinylpyrrolidone to 20 g. of Dimethicone oil (Example 2), and 70 g. of vinylpyrrolidone to 30 g. of Dimethicone oil (Example 3). Similar results to Example 1 were obtained in these runs.

EXAMPLE 4

The procedure of Example 1 was followed using a weight ratio of 20 g. of vinylpyrrolidone and 80 g. of Dimethicone oil. The resultant composition was not as viscous as in Example 1. The microdroplets obtained remained in discrete form, however, without coalescence, but settled to the bottom of the solution as a separate layer.

EXAMPLE 5

The procedure of Example 1 was followed using a weight ratio of 135 g. of vinylpyrrolidone to 15 g. of Dimethicone oil in 600 ml. of water. The results were substantially the same as obtained in Example 1.

EXAMPLE 6

The procedure of Example 1 was followed using a weight ratio of 135 g. of vinylpyrrolidone to 15 g. of a Dimethicone oil having a viscosity of 1,000 cs (mol. wt. of 28,000). The mixture was agitated at 700 rpm to produce a stable dispersion of the viscous silicone oil droplets in the aqueous polymer solution.

EXAMPLE 7

A pilot plant run was carried out in a 30 gal. reactor using two wide span turbine agitators having pitched and flat blades set at 200 rpm. 10,790 g. of vinylpyrrolidone, 1205 g. of Dimethicone oil, 100 cs, 48,225 g. of water, 120 g. of di-t-butylperoctoate, and 317 g. of Germaben ® preservative were used in this run. After 6 hours, polymerization was complete and a stable, homogeneous, milky aqueous dispersion of discrete, coated silicone oil droplets was obtained which dispersion remained in discrete and suspended form throughout the composition. The composition also was stable for an extended period of time.

EXAMPLE 8

The procedure of Example 1 was followed using 102 g. of vinylpyrrolidone, 11 g. of Dimethicone, 100 cs, 36 g. of a 50% aqueous solution of methacrylamidopropyl-trimethylammonium chloride, 462 g. of water, 0.1 g. of tetrasodium pyrophosphate, and 0.60 g. of di-tert-butylperoctoate. A stable, homogeneous composition was obtained having a residual VP content of only 0.01%.

EXAMPLE 9

The procedure of Example 1 was followed using 90 g. of vinylpyrrolidone, 10 g. of Dimethicone oil, 100 cs, 400 g. of water and 0.75 g. of Lupersol 11. The results were similar to those obtained in Example 4.

EXAMPLE 10

The procedure of Example 1 was followed 90 g. of vinylpyrrolidone, 10 g. of light mineral oil having a density of 0.838 g/ml, 400 g. of water and 0.75 g. of Lupersol 11 The results were similar to Example 1.

EXAMPLE 11

The procedure of Example 10 was followed using 10 g. of heavy mineral oil having a density of 0.862 g/ml. The results were similar to Example 10.

TABLE I

| Ex. No. | Mono-mer | Amt (g) | Silicone Oil | Amt (g) | Viscosity (cs) | MW |
|---|---|---|---|---|---|---|
| 1 | VP | 90 | DM | 10 | 100 | 5970 |
| 2 | VP | 80 | DM | 20 | 100 | 5970 |
| 3 | VP | 70 | DM | 30 | 100 | 5970 |
| 4 | VP | 20 | DM | 80 | 100 | 5970 |
| 5 | VP | 135 | DM | 15 | 100 | 5970 |
| 6 | VP | 135 | DM | 15 | 1000 | 28,000 |
| 7* | VP | 10,790 | DM | 1205 | 100 | 5970 |
| 8 | VP | 102 | DM | 11 | 100 | 5970 |
| 9 | VP | 90 | DM | 10 | 100 | 5970 |
| 10 | VP | 90 | MO | 10 | | |
| 11 | VP | 90 | MO | 10 | | |

TABLE I-A

| Ex. No. | Comonomer | Amt (g) | Medium | Amt (g) | Initiator | Amt (g) | Agitation (rpm) |
|---|---|---|---|---|---|---|---|
| 1 | — | — | Water | 400 | TBP | 0.75 | 350 |
| 2 | — | — | Water | 400 | TBP | 0.75 | 350 |
| 3 | — | — | Water | 400 | TBP | 0.75 | 350 |
| 4 | — | — | Water | 400 | TBP | 0.75 | 350 |
| 5 | — | — | Water | 600 | TBP | 0.76 | 350 |
| 6 | — | — | Water | 600 | TBP | 0.76 | 700 |
| 7* | — | — | Water | 48,225 | TBP | 120 | 200 |
| 8 | MAPTAC | 18 | Water | 462 | TBP | 0.60 | 350 |
| 9 | — | — | Water | 400 | TBPP | 0.75 | 350 |
| 10 | — | — | Water | 400 | TBP | 0.75 | 350 |
| 11 | — | — | Water | 400 | TBP | 0.75 | 350 |

*Pilot plant run

TABLE II

| Ex. No. | % Solids | Brookfield Viscosity (cps) | Diameter of Microspheres (microns) | | Form of Composition |
|---|---|---|---|---|---|
| | | | Mean | Range | |
| 1 | 19.7 | 7,200 | — | — | stable, homogeneous, milky dispersion of discrete microspherical droplets of silicone oil coated by polyvinylpyrrolidone polymer |
| 2 | 22.0 | 24,400 | | 1-14 | |
| 3 | 21.1 | 17,300 | | 1-17 | |
| 4 | 20.0 | — | | — | |
| 5 | | | | | |
| 6 | 20.6 | 10,200 | 56 | | |
| 7 | 20.2 | 8,900 | 80 | 3-54 | |
| 8 | 30.3 | 11,300 | — | — | |
| 9 | 20.2 | 7,200 | — | — | |
| 10 | 20.45 | 4,770 | — | 0.4-13 | as in Ex. 1 |
| 11 | 21.00 | 3,180 | — | 0.5-29 | as in Ex. 1 |

INDUSTRIAL APPLICABILITY

The present compositions are used in a conventional manner.

The following Examples further illustrate the preferred embodiments within the scope of the present invention. The Examples are given solely for the purposes of illustration and are not to be construed as limitations of the present invention as many variations of the invention are possible without departing from its spirit and scope.

The following examples are representative of the conditioning hair care compositions of the present invention.

TABLE A

| CONDITIONING SHAMPOO COMPOSITION | | | |
|---|---|---|---|
| Components | Concentration (%) by Weight | | |
| Essential Components | Suitable | Preferred | Optimum |
| (a) Stabilized Silicone Product (of Ex. 8, 30.3% active) | 0.25-25 | 1-10 | 2.5 |
| (b) Surfactant | 4-25 | 7-20 | 15 |
| (c) Water | qs | qs | qs |

TABLE B

| PROPERTIES OF CONDITIONING SHAMPOO COMPOSITION OF INVENTION | | | |
|---|---|---|---|
| | Composition | | |
| | Suitable | Preferred | Optimum |
| pH | 4-7.5 | 5-7 | 6 |
| Viscosity, cps | 2,000-15,000 | 3,000-8,000 | 5,000 |

The following are representative of the conditioning shampoo compositions of the present invention.

TABLE C

Weight %

| Component | I | II | III |
|---|---|---|---|
| PVP-MAPTAC-Silicone Product (30% active) (102/18/11) Ex 8 | 15.0 | 10.0 | 5.0 |
| Ammonium lauryl sulfate (30% active) | 30.9 | 30.0 | 30.5 |
| Lauric Diethanolamide (100% active) | 5.0 | 5.0 | 5.0 |
| Preservative | 0.5 | 0.5 | 0.5 |
| Fragrance | 0.2 | 0.2 | 0.2 |
| Water | qs | qs | qs |

The conditioning shampoo compositions of the invention exhibit excellent properties in actual use on hair including effective curl retention, enhanced hair stiffness, and advantageous curl snap, in direct comparative testing with other related products having silicone dispersed therein.

| AEROSOL CONDITIONING AND STYLING MOUSSE | | | |
|---|---|---|---|
| Essential | Suitable | Preferred | Optimum |
| PVP-MAPTAC-Silicone (102/18/11, Ex. 8) (30% Active) | 0.5–10 | 1–5 | 3.0 |
| Resin (Gaffix ® VC-713, GAF) | 1–10 | 2–8 | 5.0 |
| Surfactant (non-ionic, nonoxynol-9 or sodium cocoylisethionate) | 0.1–5 | 0.2–1 | 0.5 |
| Water | qs | qs | qs |
| Propellant (A-46, isobutane/propane) | 5–25 | 10–20 | 15.0 |

The following is a specific example of the conditioning mousse of the invention.

| Ingredient | % by weight |
|---|---|
| PVP-MAPTAC-Silicone (Ex. 8) (30% solids) | 3.0 |
| Vinylpyrrolidone/dimethylaminoethyl methacrylate quaternized w/diethylsulfate | 5.00 |
| Oleth-20 | 0.5 |
| Fragrance | 0.25 |
| Propellant A-46 | 15.0 |
| DM DM Hydantoin | 0.25 |
| Deionized water | 76.0 |
| | 100.00 |

The expansion properties of the foam in the mousse composition is enhanced by the presence of the PVP-MAPTAC-silicone therein. In addition, the texture and feel of the foam is smoother with the PVP-MAPTAC-silicone present. Furthermore the mousse is effective for mending split ends of hair.

| CONDITIONER COMPOSITION | | | |
|---|---|---|---|
| | Suitable | Preferred | Optimum |
| PVP-MAPTAC-Silicone (Ex. 8) (30% solids) | 0.5–10 | 1–5 | 2.5 |
| Emulsifier/thickener | 1–10 | 2–7 | 3.5 |
| Cationic surfactant | 0–10 | 2–5 | 3.0 |
| Water | qs | qs | qs |

The conditioner composition is effective to mend split ends of hair.

| Ingredient | % by weight |
|---|---|
| Emulsifying wax | 3.5 |
| Stearyl alcohol + Ceteareth-20 | 1.5 |
| Glycol stearate | 0.5 |
| PVP/MAPTAC/Silicone (Ex. 8) | 2.5 |
| Laneth-16 + Ceteth-16 + Oleth-16 + Steareth-16 | 0.3 |
| Methylparaben | 0.2 |
| Propylparaben | 0.1 |
| Water | qs |

The following examples are representative of cosmetic compositions of the present invention.

| LOTION FOR DRY SKIN | | | |
|---|---|---|---|
| Essential | Suitable | Preferred (% by Wt.) | Optimum |
| PVP-MAPTAC-Silicone (Ex. 8) (30% solids) | 0.5–10 | 1–5 | 3.0 |
| Stabilizer | 0.05–0.5 | 0.1–0.3 | 0.15 |
| Emulsifier | 1–10 | 2–8 | 3.0 |
| Soap | 1–10 | 2–8 | 3.0 |
| Wx | 0–10 | 3–8 | 5.0 |
| Neutralizer | 0.2–1 | 0.4–1 | 1.0 |
| Water | qs | qs | qs |

The following is a specific example of a lotion for dry skin composition of the invention

| Ingredient | % by weight |
|---|---|
| Distilled water | 85.10 |
| Polyacrylic acid (crosslinked) | 0.15 |
| Stearic acid, XXX | 3.00 |
| Mineral oil, 70 cts | 2.00 |
| Emulsifying wax | 3.00 |
| PVP-MAPTAC-Silicone (Ex. 8) (30% solids) | 3.00 |
| Oleth-20 | 1.50 |
| Triethanolamine | 1.00 |
| Methylparaben/propylparaben | 1.00 |
| Fragrance | 0.25 |
| | 100.00 |

The presence of the PVP-silicone in the lotion enhances the smoothness, softness and silky feel of the skin.

| SUNSCREEN LOTION (1) | |
|---|---|
| PVP-MAPTAC-Silicone (Ex. 8) | 2.5 |
| sorbitol | 6.0 |
| propylparaben | 0.1 |
| glyceryl stearate | 2.4 |
| stearic acid | 1.5 |
| octyl dimethyl PABA | 7.5 |
| benzophenone-3 | 2.5 |
| lanolin | 2.5 |
| methylparaben | 0.2 |
| deionized water | qs |

| SKIN CLEANSER FOR OILY SKIN | |
|---|---|
| PVP-MAPTAC-Silicone (Ex. 8) | 2.5 |
| propylene glycol | 5.0 |
| hydroxyethylcellulose | 0.9 |
| sodium laureth sulfate (30% active) | 15.0 |
| preservative | 0.75 |
| germacidal agent | 6.0 |
| water | qs |

| MOISTURIZING LOTION | |
|---|---|
| PVP-MAPTAC-Silicone (Ex. 8) | 2.0 |
| mineral oil 70 CTS | 2.0 |
| stearic acid | 3.0 |
| emulsifying wax | 3.0 |
| Dimethicone* 200 CTS | 1.5 |
| Carbomer 934** | 0.15 |
| Oleth-20*** | 1.0 |
| triethanolamine 98% | 1.0 |
| deionized water | qs |
| preservative | qs |

-continued

| MOISTURIZING LOTION | |
|---|---|
| fragrance | qs |

*a mixture of methylated siloxane polymers end-blocked with trimethyl siloxy units (dimethylpolysiloxane)
**cross-linked polymer of acrylic acid
***PEG ether of oleyl alcohol

| CATIONIC MOUSSE HAND/BODY LOTION (Used 85 Parts of the following formula to 15 parts propellant A-46) | |
|---|---|
| PVP-MAPTAC-Silicone (Ex. 8) | 0.50 |
| acetylated polyoxyethylene lanolin | 2.00 |
| ethoxylated lanolin alcohols | 1.00 |
| glyceryl stearate, self-emulsifying | 5.50 |
| cetyl alcohol | 1.50 |
| mineral oil, 70 CTS | 1.50 |
| stearyl alcohol | 1.50 |
| glycerin | 3.00 |
| isopropyl myristate | 4.00 |
| dimethicone, 100 CTS | 2.00 |
| water | qs |
| preservative | qs |
| fragrance | qs |

What is claimed is:

1. A hair or skin care composition containing a stabilized cosmetically-active product obtained by in situ copolymerization of a water-soluble vinyl monomer and an acryl comonomer in the presence of discrete microdroplets of a cosmetically-active oil in water.

2. A hair or skin care composition according to claim 1 wherein said water-soluble vinyl monomer is vinyl pyrrolidone and said acryl comonomer is methacrylamidopropyltrimethylammonium chloride.

3. A hair or skin care composition according to claim 2 wherein the weight ratio of the vinylpyrrolidone monomer to silicone in the copolymerization mixture is about 95:5 to 5:95, respectively, on a weight basis.

4. A hair or skin care composition according to claim 2 wherein the Brookfield viscosity of the stabilized oil in water product obtained upon in situ copolymerization is about 3,000 to 100,000 cps.

5. A hair or skin care composition according to claim 1 wherein said stabilized microdroplets are homogeneously distributed throughout the resulting copolymer solution and said cosmetically-active oil is a silicone having a viscosity between about 5 to 600,000 cs.

6. A hair or skin care composition according to claim 5 wherein said silicone is a non-volatile polyalkyl siloxane, a polyaryl siloxane, a polyalkylaryl siloxane or a polyether siloxane.

7. A skin care composition according to claim 6 wherein said silicone oil is a polydimethyl siloxane.

8. A hair or skin care composition according to claim 1 wherein said product is present in an amount of about 0.1 to 25 weight percent of the composition.

9. A hair or skin care composition according to claim 8 wherein said amount is about 1 to 10 weight percent of the composition.

10. A conditioning hair care composition according to claim 1 wherein said water-soluble vinyl monomer is vinyl pyrrolidone and said acryl comonomer is methylacrylamidopropyltrimethyl ammonium chloride.

11. A skin care composition according to claim 1 which is a lotion for dry skin.

12. A skin care composition according to claim 1 which is a cationic mousse hand/body lotion.

13. A skin care composition according to claim 1 which is a sunscreen formulation.

14. A skin care composition according to claim 1 which is a moisturizing lotion.

15. A conditioning hair care composition comprising
(a) a stabilized silicone product obtained by in situ copolymerization of a water-soluble vinyl monomer and a water-soluble acryl comonomer in the presence of discrete micordroplets of a silicone in water,
(b) a surfactant, and the balance being
(c) water.

16. A hair care composition according to claim 15 which is a conditioner composition.

17. A hair care composition according to claim 15 which is an aerosol conditioning mousse.

* * * * *